United States Patent [19]

Marciel

[11] Patent Number: Plant 6,875

[45] Date of Patent: Jun. 27, 1989

[54] MINIATURE ROSE NAMED DEVROSADO

[75] Inventor: Stanley G. Marciel, Freedom, Calif.

[73] Assignee: DeVor Nurseries, Inc., Freedom, Calif.

[21] Appl. No.: 174,522

[22] Filed: Mar. 28, 1988

[51] Int. Cl.[4] ..... A01H 5/00

[52] U.S. Cl. ..... Plt./9

[58] Field of Search ..... Plt. 9

*Primary Examiner*—Robert E. Bagwill

*Attorney, Agent, or Firm*—Charles W. Rummler

[57] ABSTRACT

A new bright pink miniature rose distinguished by its continuous and profuse year around production of small flowers of about one and one-half inch diameter (40 mm.) with petals in a whorled-imbricated arrangement borne singly on strong, generally upright stems freely branching from the stalk of an abundantly leaved plant having a total height of about six and one-half inches (160 mm.) and by the long lasting quality of the blooms both on the plant and as a cut flower.

1 Drawing Sheet

BACKGROUND OF THE INVENTION

This new miniature rose plant was produced in 1986 at Pleasanton, Calif., as a result of breeding efforts carried on by me since about 1984 with the object of developing an improved miniature rose particularly suited to pot plant culture, the new plant being a seedling resulting from my crossing of an unnamed and unpatented plant bearing the number K-103-KET as the seed parent with pollen from the miniature rose plant 'Orange Sunblaze' (unpatented) at Pleasanton and this new plant was asexually reproduced by me at Pleasanton by its own roots and several generations of the new plant so propagated have shown that its distinctive and novel characteristics hold true from generation to generation and appear to be firmly fixed. Commercial propagation of this new plant by its own roots is now being done on a commercial scale at Pleasanton and also at Watsonville, Calif.

DESCRIPTION OF THE DRAWING

My new miniature rose plant is illustrated by the accompanying photographic drawing, in which the uppermost view is a potted plant of the new variety in full bloom and the lower view shows parts of the new plant, including a flower stem with leaves and a flower but about to open to a fully developed bloom, top side and bottom side views of a typical leaf of this plant, a typical calyx with the petals removed showing the sepals, and face views of a pair of fully opened flowers of the new plant, the right hand one being as faded after about four days; the colors shown in all views being as nearly true to those herein specified as is possible to obtain by professional photographic procedures.

DESCRIPTION OF THE NEW VARIETY

The following is a detailed description of my new miniature rose plant based upon observations of plants grown in greenhouse both at Pleasanton and at Watsonville, Calif., the color designations being according to The R.H.S. Colour Chart published by The Royal Horticultural Society of London, England.

THE PLANT

Origin: Seedling.

Parentage:

*Seed parent.*—Stock Variety No. K-103-KET maintained at Pleasanton, Calif.

*Pollen parent.*—Miniature rose named 'Orange Sunblaze' (unpatented).

Classification: Miniature Rose Plant.

Form: Small, compact bush.

Growth rate: Vigorous and very sturdy for a small mini-flora bush.

Height: About 160 mm.

Cane length: About 135 mm.

Color: Yellow-Green, 144 B.

Growth habit: Free branching, compact and vigorous.

Foliage:

*Quantity.*—Abundant.

*Number of leaves.*—About 5 to 7 from hook on the flower stem.

*Margin type.*—Serrate.

*Number of leaflets.*—3 to 7.

*Size of leaf.*—3 leaflet — About 85 mm. long and about 56 mm. wide. 7 leaflet — About 93 mm. long and about 62 mm. wide.

*Texture.*—Smooth.

*Aspect.*—Slightly glossy.

*Color.*—Upper side — Green, 137 C. Under side — Green, 138 B.

*Ribs and veins.*—The rib is prominent and the veins show slightly.

*Petiolule.*—About 1 mm.

*Petioles.*—About 18 mm. long.

Thorns: The plant has thorns but they are sparse.

*Size.*—About 4 mm. long.

*Color.*—Greyed Purple, 184 C.

THE BUD

Size: Small.

Shape: Ovoid and pointed.

Rate of opening: Moderately slow.

Color of petals:

*When sepals first divide.*—Red, 55 B.

*When the petals begin to unfurl.*—Red, 55 B.

Sepals:

*Number.*—Five.

*Shape.*—Linear with acuminate tip and one sepal per bud is usually foliacious.

*Character.*—The sepals are hooded over the bud and when the flowers open, the sepals curl back and stand outwardly.

*Color.*—Inside: Outer edge to tip — Green, 138 B, with a center of Green, 138 C. Outside: Outer edge to tip — Green, 144 A. Center — 144 B.

Calyx:

*Shape.*—Funnel-shaped.

*Size.*—Small.

*Aspect.*—Smooth.

Peduncle or flower stem:

*Length.*—About 30 mm. when sepals curl back.

*Hairs.*—Hairy.

*Character.*—Erect, sturdy and slender.

*Color.*—Yellow-Green, 144 B, with a slightly reddish tinge.

THE FLOWER

Blooming habit: Profusely and continuously the year around under glass, blooming freely in the Fall.

Size: Small.

*Diameter.*—About 40 mm. when fully opened.

*Depth.*—About 18 mm.

Borne: Singly.

Shape: When bloom first opens, high centered. When bloom matures, the petals reflex slightly.

Petalage:

*Number.*—32.

*Arrangement.*—Imbricated.

*Form.*—Abrupt point.

*Margins.*—Smooth.

*Texture.*—Soft.

*Aspect.*—Satiny.

*Color.*—Outer petals: Body — Red, 52 C. Base — White, 155 C. Color measurement — About 13 mm. of 52 C. Reverse side — Red, 55 B. Base — White, 155 C. Color measurement — About 13 mm. of 55 B. Inside petals: Body — Red, 52 C. Base — White, 155 C. Color measurement — 8 mm. Reverse side — Red, 55 C. Base — White, 155 C. Color measurement — About 18 mm. The white continues in a streak along the midrib of the petal to the tip.

*Color change.*—The blossom color changes from 52 C to 52 D in about four days.

Petaloids:

*Number.*—Three.

*Size.*—About 4 to 9 mm.

*Color.*—Red, 52 C; base White, 155 C.

Flower stem:

*Length.*—About 30 mm.

*Character.*—Sturdy and upright.

*Color.* 13 Yellow-Green, 144 B.

Persistence: The flowers hang on and dry.

Fragrance: Slightly spicy.

Lasting quality: Long lasting both on the plant and as a cut flower.

Disease resistance: Moderately resistant to mildew, rust and black spot, as observed in greenhouse at Pleasanton and at Watsonville, Calif.

THE REPRODUCTIVE ORGANS

Stamens:

*Number.*—30.

*Arrangement.*—Slightly introrsed.

*Anthers.*—Size: About 2 mm. Color: Yellow-Orange, 22 C.

*Filaments.*—Length: About 3 mm. Color: Yellow-Orange, 20 C.

*Pollen.*—Color: Yellow-Orange, 22 C.

Pistils:

*Number.*—17.

*Styles.*—Length: About 4 mm. Color: Yellow, 4 D.

*Stigmas.*—Color: Red, 41 C.

Character of ovaries: Dome shaped, styles unattached to each other throughout; a few silver hairs.

This miniature rose is an attractive plant with bright pink blooms covering lush foliage and presenting a full, well balanced appearance.

I claim:

1. The new and distinct variety of miniature rose plant and parts thereof substantially as herein shown and described, characterized by the profuse and continuous production of small pink flowers borne on the sturdy, upright stems of a free-branching plant having abundant foliage and an average height of about 160 mm.

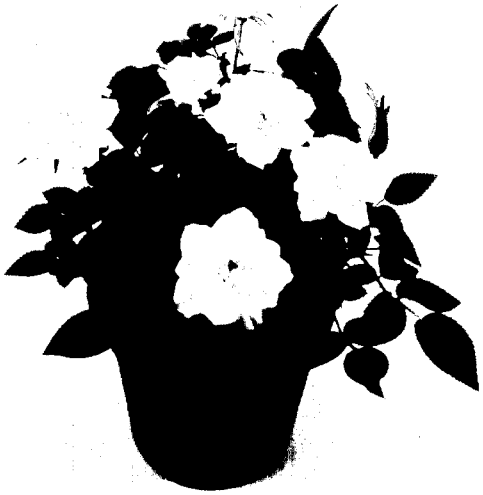
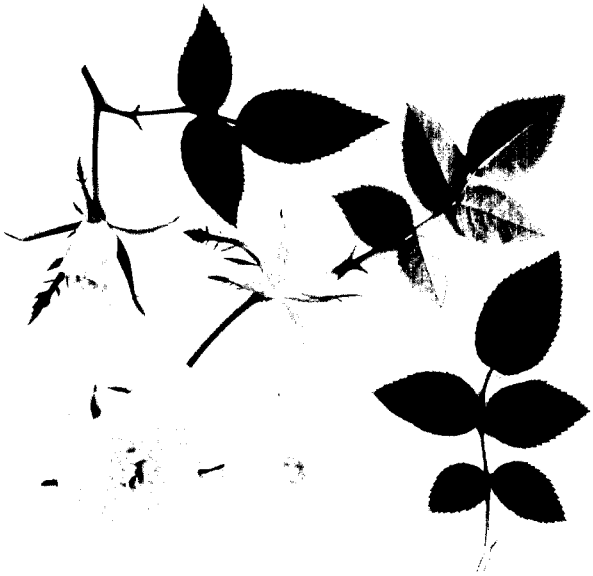

* * * * *